US012599498B2

(12) United States Patent
Rapoport

(10) Patent No.: US 12,599,498 B2
(45) Date of Patent: Apr. 14, 2026

(54) AUTOMATED IMAGE GUIDANCE FOR OPHTHALMIC SURGERY

(71) Applicant: Alcon Inc., Fribourg (CH)

(72) Inventor: Tobias Jura Rapoport, Berlin (DE)

(73) Assignee: ALCON INC., Fribourg (CH)

( * ) Notice: Subject to any disclaimer, the term of this patent is extended or adjusted under 35 U.S.C. 154(b) by 419 days.

(21) Appl. No.: 18/463,121

(22) Filed: Sep. 7, 2023

(65) Prior Publication Data

US 2024/0082056 A1     Mar. 14, 2024

Related U.S. Application Data

(60) Provisional application No. 63/405,737, filed on Sep. 12, 2022.

(51) Int. Cl.
| | |
|---|---|
| *A61F 9/007* | (2006.01) |
| *A61B 3/14* | (2006.01) |
| *G06F 3/01* | (2006.01) |
| *G06V 20/52* | (2022.01) |
| *G06V 40/18* | (2022.01) |
| *H04N 5/265* | (2006.01) |

(52) U.S. Cl.
CPC ................ *A61F 9/007* (2013.01); *A61B 3/14* (2013.01); *G06F 3/013* (2013.01); *G06V 20/52* (2022.01); *G06V 40/193* (2022.01); *H04N 5/265* (2013.01)

(58) Field of Classification Search
CPC ........ A61F 9/007; A61F 9/00736; A61B 3/14; A61B 90/20; A61B 2034/2065; A61B 2090/365; A61B 3/13; A61B 3/0058;
G06F 3/013; G06V 20/52; G06V 40/193; H04N 5/265; G06T 2207/10056; G06T 2207/30041; G06T 7/33; G06N 20/00
USPC ......................................................... 351/206
See application file for complete search history.

(56) References Cited

U.S. PATENT DOCUMENTS

| | | | |
|---|---|---|---|
| 2009/0073386 A1 | 3/2009 | Petito | |
| 2011/0251483 A1 | 10/2011 | Razzaque | |
| 2016/0183779 A1* | 6/2016 | Ren | A61B 90/20 |
| | | | 351/246 |
| 2018/0041699 A1 | 2/2018 | Tohara | |
| 2022/0346884 A1* | 11/2022 | Leiderman | G06V 40/18 |
| 2023/0334678 A1* | 10/2023 | Yin | G06T 7/0014 |

FOREIGN PATENT DOCUMENTS

| | | | |
|---|---|---|---|
| JP | 2018023026 A | 2/2018 | |
| WO | WO-2021149056 A1 * | 7/2021 | A61F 9/007 |

* cited by examiner

*Primary Examiner* — Mohammed A Hasan

(57) ABSTRACT

In certain embodiments, an ophthalmic system and computer-implemented method for automatically initializing an image guided surgery are described. The initialization includes monitoring a scene using multiple images captured by a first imaging device. An eye of a user is detected within a first image of the multiple images. In response to detecting the eye of the user, a registration procedure is initiated with the first image and a reference image of the eye of the user to generate a set of transformation information. A set of overlay content is generated based on the set of transformation information. The set of overlay content includes a transformed first image or a transformed reference image. Overlay content is presented onto the scene via a second imaging device.

20 Claims, 5 Drawing Sheets

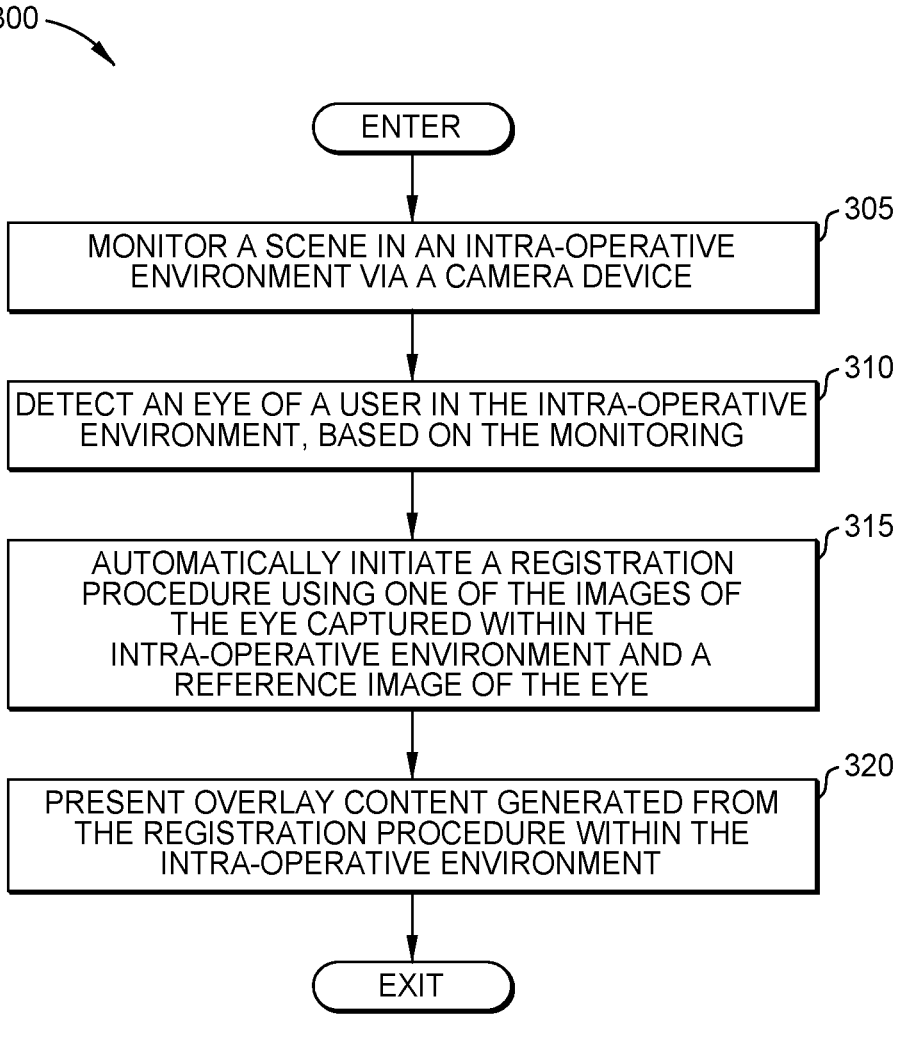

300

ENTER

MONITOR A SCENE IN AN INTRA-OPERATIVE
ENVIRONMENT VIA A CAMERA DEVICE          305

DETECT AN EYE OF A USER IN THE INTRA-OPERATIVE
ENVIRONMENT, BASED ON THE MONITORING          310

AUTOMATICALLY INITIATE A REGISTRATION
PROCEDURE USING ONE OF THE IMAGES OF
THE EYE CAPTURED WITHIN THE
INTRA-OPERATIVE ENVIRONMENT AND A
REFERENCE IMAGE OF THE EYE          315

PRESENT OVERLAY CONTENT GENERATED FROM
THE REGISTRATION PROCEDURE WITHIN THE
INTRA-OPERATIVE ENVIRONMENT          320

EXIT

FIG. 3

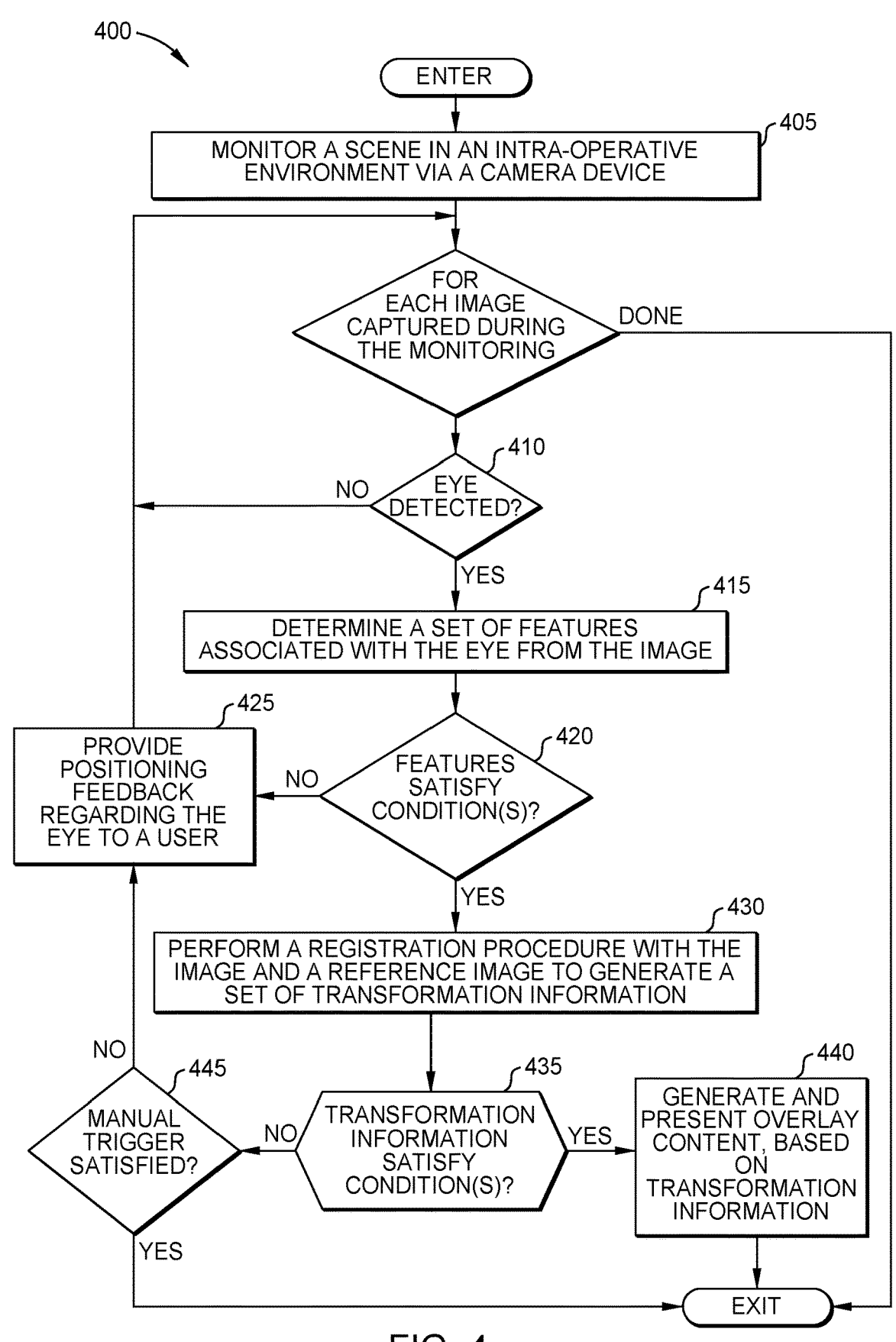

400

ENTER

MONITOR A SCENE IN AN INTRA-OPERATIVE
ENVIRONMENT VIA A CAMERA DEVICE ⌐405

FOR
EACH IMAGE
CAPTURED DURING          DONE
THE MONITORING

410

NO          EYE
DETECTED?

YES

DETERMINE A SET OF FEATURES
ASSOCIATED WITH THE EYE FROM THE IMAGE ⌐415

PROVIDE
POSITIONING
FEEDBACK          NO          FEATURES          420
REGARDING THE                    SATISFY
EYE TO A USER          CONDITION(S)?

425          YES

PERFORM A REGISTRATION PROCEDURE WITH THE
IMAGE AND A REFERENCE IMAGE TO GENERATE A
SET OF TRANSFORMATION INFORMATION ⌐430

NO          435          440

MANUAL          NO          TRANSFORMATION          GENERATE AND
TRIGGER                    INFORMATION          YES          PRESENT OVERLAY
SATISFIED?          SATISFY          CONTENT, BASED
CONDITION(S)?          ON
TRANSFORMATION
445          INFORMATION

YES

EXIT

FIG. 4

AUTOMATED IMAGE GUIDANCE FOR OPHTHALMIC SURGERY

BACKGROUND

Image guidance generally refers to any form of medical imaging to plan, perform, and evaluate surgical procedures, including but not limited to, ophthalmic microsurgical procedures (e.g., vitreoretinal procedures, such as retinotomies, retinectomies, autologous retinal transplants, etc., and anterior segment surgery procedures, such as cataract surgery, minimally invasive glaucoma surgery (MIGS), etc.). For example, image guidance can involve tracking and guiding instruments (e.g., lasers, probes, etc.) in real-time during a surgical procedure, providing visual feedback to a surgeon (or physician) performing the surgical procedure, supporting manual execution of a treatment via visual aids (e.g., augmented reality using a surgical microscope), and the like.

SUMMARY

In certain embodiments, an ophthalmic system is provided. The ophthalmic system includes a first imaging device, a second imaging device, a memory comprising executable instructions, and a processor in data communication with the memory. The first imaging device is adapted to capture a plurality of images of a scene within an intra-operative environment. The second imaging device is adapted to visualize the scene. The processor is configured to execute the executable instructions to monitor the scene using the plurality of images captured by the first imaging device. The processor is also configured to execute the executable instructions to, upon detecting an eye of a user within a first image of the plurality of images, automatically initialize an image-guided surgery, comprising initiating a registration procedure to generate a set of transformation information, based at least in part on the first image and a reference image of the eye of the user. The processor is also configured to execute the executable instructions to generate a set of overlay content based on the set of transformation information, wherein the set of overlay content comprises (i) a transformed first image or (ii) a transformed reference image. The processor is further configured to execute the executable instructions to present the overlay content onto the scene via the second imaging device.

In certain embodiments, a computer-implemented method is provided. The computer-implemented method includes monitoring a scene in an intra-operative environment using a plurality of images captured by a first imaging device. The computer-implemented method also includes, upon detecting an eye of a user within a first image of the plurality of images, automatically initializing an image-guided surgery, wherein automatically initializing the image-guided surgery comprises initiating a registration procedure to generate a set of transformation information, based at least in part on the first image and a reference image of the eye of the user. The computer-implemented method further includes generating a set of overlay content based on the set of transformation information, wherein the set of overlay content comprises (i) a transformed first image or (ii) a transformed reference image. The computer-implemented method further includes presenting the overlay content onto the scene via a second imaging device.

In certain embodiments, a non-transitory computer-readable medium is provided. The non-transitory computer-readable medium has computer executable instructions stored thereon. The computer executable instructions are executable by one or more processors to perform an operation. The operation includes monitoring a scene in an intra-operative environment using a plurality of images captured by a first imaging device. The operation also includes, upon detecting an eye of a user within a first image of the plurality of images, automatically initializing an image-guided surgery, wherein automatically initializing the image-guided surgery comprises initiating a registration procedure to generate a set of transformation information, based at least in part on the first image and a reference image of the eye of the user. The operation further includes generating a set of overlay content based on the set of transformation information, wherein the set of overlay content comprises (i) a transformed first image or (ii) a transformed reference image. The operation further includes presenting the overlay content onto the scene via a second imaging device.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

FIG. 3 is a flowchart of a method for automatically initializing an image guided surgery, according to certain embodiments.

FIG. 4 is a flowchart of another method for automatically initializing an image guided surgery, according to certain embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Figure 1:
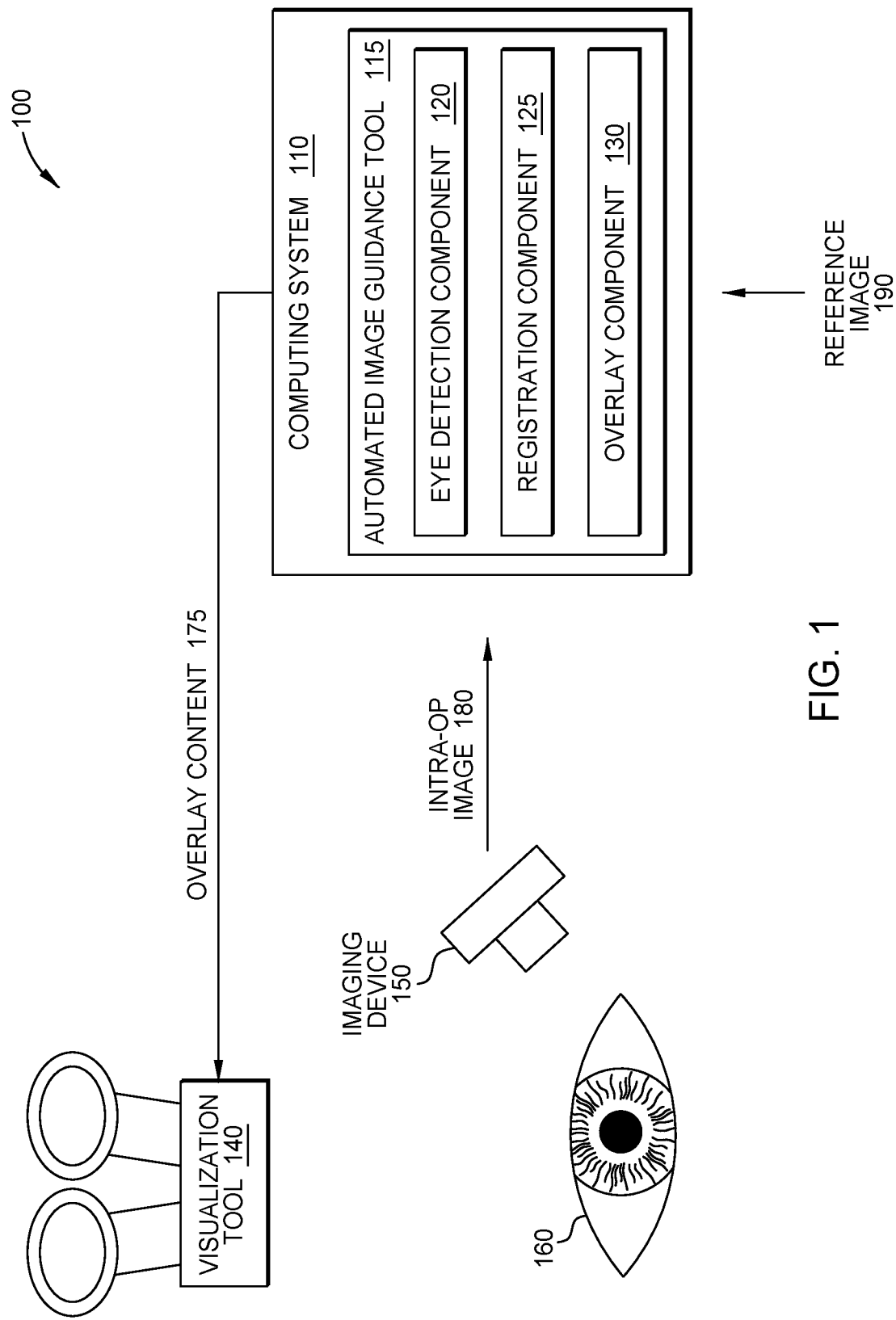
FIG. 1 illustrates an example ophthalmic system for automatically initializing an image guided surgery, according to certain embodiments.

A crucial component of image guidance systems, especially in an ophthalmic surgical setting, is the ability to register one or more pre-operative images of a patient with one or more intra-operative images of the patient. For example, during image registration, different image datasets are generally transformed into one coordinate system with matched imaging contents (or features). Image registration can be a computer-aided process where features in the intra-operative image(s) are detected based on a pre-defined description, e.g., pattern matching for manual markings, registration against a pre-operative image (also referred to as a reference image), etc. The establishment of image correspondence through image registration is crucial to many clinical tasks, including but not limited to, ophthalmic microsurgical procedures, etc. For example, images transformed as a result of image registration may be used during the surgical procedure (e.g., in real-time) to help orient the surgeon regarding the location of various features/structures associated with the patient's eye.

One issue with conventional image guidance systems is that they generally rely on the surgeon (or another medical operator) to manually initialize the image guided surgery, e.g., by manually triggering the image registration procedure. For example, an exemplary conventional image guidance system may include an initial alignment step in which the surgeon has to position the eye under a microscope. Once the surgeon is satisfied with the position of the patient's eye, the surgeon generally has to manually press a button in order to trigger the image guidance system to attempt the image registration. This manual intervention by the surgeon creates an additional step that requires time and attention and may distract the surgeon from the actual surgical procedure at hand. Additionally, relying on manual intervention by the surgeon to initialize the image guidance may involve additional input devices (e.g., foot pedals, touch screens, etc.), which can occupy space in the operating room and/or even involve additional non-sterile equipment (e.g., circulator) to operate the input devices. Thus, it is desirable to provide techniques, systems, and devices for automatically initializing an image guidance operation for a surgical procedure (e.g., an image guided surgery).

Embodiments described herein provide systems, techniques, and devices for performing an automatic initialization of an image guided surgery. The automatic initialization may include automatically initiating an image registration of an intra-operative image of a patient's eye with a reference image, such as a pre-operative image, of the patient's eye. In certain embodiments, the automatic initiation of the image registration may reduce (or full remove) manual interactions that are typically required to start an image guided surgery.

In an exemplary embodiment, an ophthalmic system includes an imaging device (e.g., camera) and a visualization tool (e.g., surgical microscope). The ophthalmic system may monitor (via the imaging device) an intra-operative scene under the visualization tool and automatically trigger an initialization of the image guidance for a surgical procedure once a patient's eye is detected in the intra-operative scene. For example, the ophthalmic system may trigger the initialization by automatically initiating a computer-aided image registration of an intra-operative image (captured via the imaging device) and a reference image (e.g., a pre-operative image of the patient's eye), without any user input.

The ophthalmic system may generate overlay content, based on the image registration, and present the overlay content to the surgeon via the visualization tool. For example, the overlay content may include a transformed reference image and/or a transformed intra-operative image that is displayed as an overlay onto the field-of-view (FOV) of the visualization tool. The display of the overlay may provide the surgeon with the pre-op information regarding the eye as the surgeon is viewing the eye via the visualization tool, thereby improving the safety and/or effectiveness of a surgical procedure. For example, the overlay content can be used for patient verification, left/right eye check, image guidance, etc.

Additionally or alternatively, in certain embodiments, the ophthalmic system may provide feedback to the surgeon via the visualization tool regarding the appropriate centration, magnification, and focus of the patient's eye. Such feedback may be provided during the monitoring of the scene and may be provided via augmented reality in the FOV of the surgeon through the visualization tool.

As such, certain embodiments of the ophthalmic system described herein can reduce or fully remove manual interactions that are typically required by conventional systems to start an image guided surgery. By reducing or removing these manual interactions, the embodiments described herein can significantly improve the surgeon's experience during a surgical procedure, lower the barrier to adoption of image guidance technology, reduce time and/or space associated with performing image guided surgery, etc.

As used herein, a hyphenated form of a reference numeral refers to a specific instance of an element and the un-hyphenated form of the reference numeral refers to the collective element. Thus, for example, device "12-1" refers to an instance of a device class, which may be referred to collectively as devices "12" and any one of which may be referred to generically as a device "12".

FIG. 1 illustrates an example ophthalmic system 100 for performing automated image guidance surgery, according to certain embodiments. The ophthalmic system 100 includes an imaging device 150, computing system 110, and a visualization tool 140. The imaging device 150 is representative of a variety of imaging devices that can capture an image of a surgical scene. An example imaging device 150 is a digital camera and other imaging devices, now known or later developed. The computing system 110 is representative of a variety of computing systems (or devices), including, for example, a laptop computer, mobile computer (e.g., a tablet or a smartphone), a server computer, a desktop computer, an imaging system, a system embedded in a medical device, etc.

The visualization tool 140 is representative of an intra-operative (intra-op) imaging device that is used during a surgical procedure in the operating room to generate imaging of patient's eye 160. An example visualization tool 140 is a digital microscope (e.g., a three-dimensional (3D) stereoscopic digital microscope), a digital camera, a digital fundus camera, analog microscope with separate or integrated displays, a monitor(s), a heads-up display(s), augmented reality device using overlay injection, and other imaging devices, now known or later developed. The computing system 110 includes an automated image guidance tool 115, which is generally configured to automatically initialize an image guidance for a surgical procedure. The automated image guidance tool 115 includes an eye detection component 120, a registration component 125, and an overlay component 130, each of which can include hardware components, software components, or combinations thereof.

In certain embodiments, the automated image guidance tool 115 monitors a scene for a patient's eye 160 via the imaging device 150, and determines whether to automatically trigger an initialization of an image guidance for a surgical procedure based on the monitoring. For example, the imaging device 150 may continuously capture one or more intra-op images 180 of the scene and send the intra-op image(s) 180 to the automated image guidance tool 115. In certain embodiments, the automated image guidance tool 115 evaluates the intra-op image(s) 180 using one or more predefined criteria and selects at least one of the intra-op image(s) 180 that satisfies a predetermined condition. For example, the automated image guidance tool 115 may select an intra-op image 180 in which the patient's eye 160 is detected.

In certain embodiments, after selecting an intra-op image 180, the automated image guidance tool 115 automatically initializes an image guidance for a surgical procedure, based at least in part on the intra-op image 180. In an exemplary embodiment, the automated image guidance tool 115 initializes the image guidance by automatically attempting an image registration of the intra-op image 180 and the reference image 190, using the registration component 125. The intra-op image 180 and the reference image 190 may include different views of the eye. The different views within the intra-op image 180 and the reference image 190 may be due, in part, to the intra-op image 180 and the reference image 190 being captured at different times, at different viewpoints, using different modalities, etc. In the depicted embodiment, the reference image 190 is an image of the patient's eye 160 captured during a pre-op phase, and the intra-op image 180 is an image of the patient's eye 160 captured during an intra-op phase. In another example, the reference image 190 and intra-op image 180 may be captured during cyclorotation of the eye as the patient changes from a sitting position to a supine position during surgery.

In certain embodiments, the reference image 190 includes one or more annotations (or markings) made by a user, such as a surgeon or surgical staff member. For example, during the pre-op phase, the user may assess clinical properties of the eye, based on the reference image 192, and annotate the reference image 190 with information associated with the clinical properties.

In certain embodiments, the automated image guidance tool 115 generates a set of transformation information for transforming the reference image 190 into the coordinate system of the intra-op image 180 or transforming the intra-op image 180 into the coordinate system of the reference image 190, based on the image registration. For example, the set of transformation information can include translation information, scaling information, and/or rotation information for at least one of the intra-op image 180 or reference image 190.

In certain embodiments, the automated image guidance tool 115 generates overlay content 175 (using the overlay component 130), based on the transformation output from the image registration. The overlay content 175 may include a transformed intra-op image, a transformed reference image 190, and/or additional information related to the reference image 190 and/or intra-op image (e.g., patient data, treatment data, etc.). The automated image guidance tool 115 sends the overlay content 175 to the visualization tool 140, which may display (or present) the overlay content 175 in the user's FOV through the visualization tool 140. In certain embodiments, the overlay content 175 may include selected features from the intra-op image 180 and/or reference image 190 that can be used to verify the expected patient and/or perform a left/right eye check. Note the eye detection component 120, registration component 125, and overlay component 130 are described in greater detail below with respect to FIG. 2.

Note that FIG. 1 illustrates a reference example of an ophthalmic system for performing automatic initialization of an image guided surgery and that, in other embodiments, the ophthalmic system may have different configurations. For example, while FIG. 1 depicts the computing system 110 as separate from the imaging device 150, in certain embodiments, the computing system 110 may be a part of the imaging device 150. Similarly, while FIG. 1 depicts the computing system 110 as separate from the visualization tool 140, in certain embodiments, the computing system 110 may be a part of the visualization tool 140. Similarly, while FIG. 1 depicts the imaging device 150 and visualization tool 140 as separate devices, in certain embodiments, the operations of the imaging device 150 and visualization tool 140 may be implemented by a single device (e.g., a digital microscope that includes optical components (such as an objective) and a digital camera to output an image). Further yet, in certain embodiments, the computing system 110, imaging device 150, and the visualization tool 140 may be a part of a single computing device (or system) that performs automatic initialization of an image guided surgery.

Figure 2:
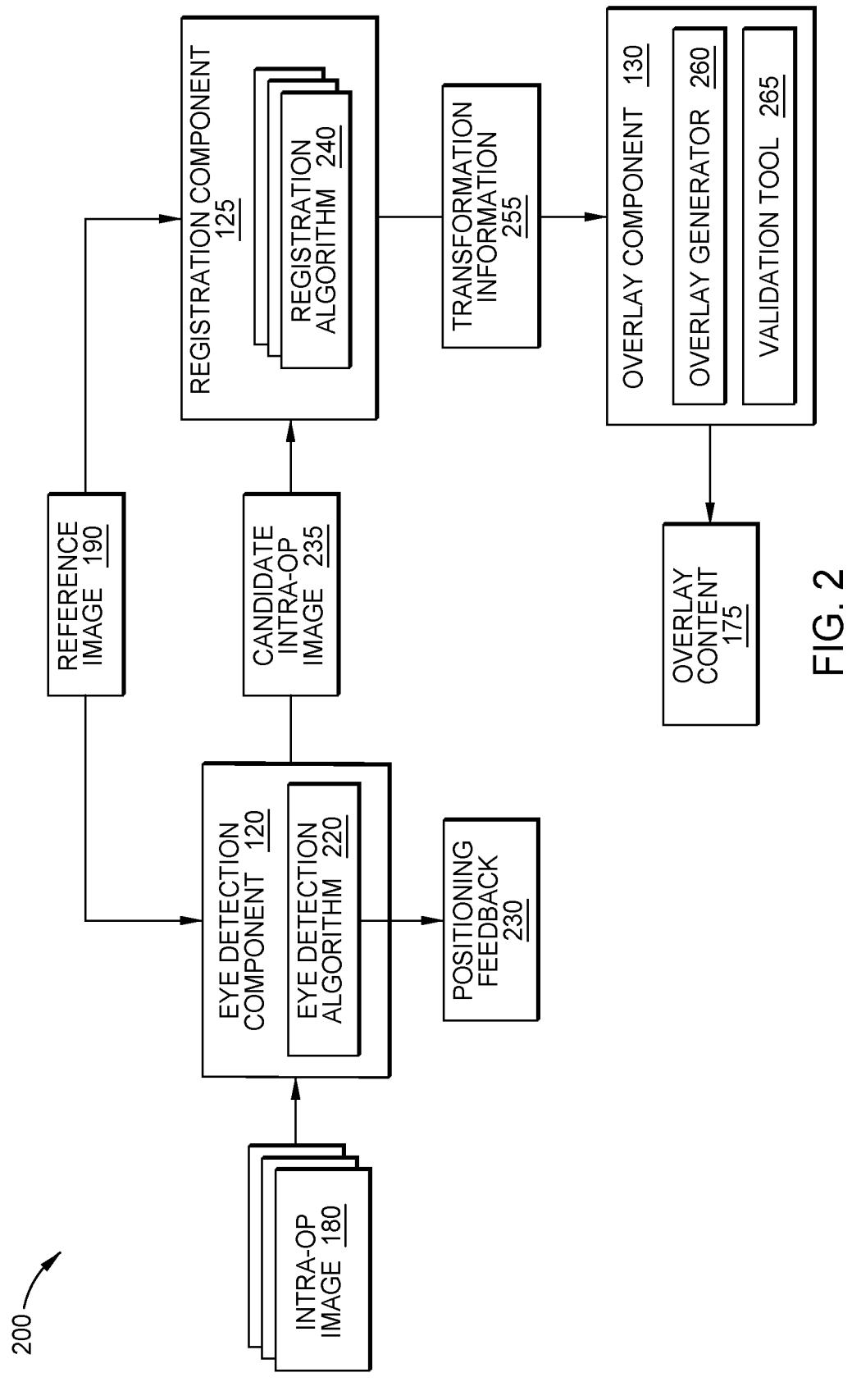
FIG. 2 illustrates an example workflow for automatically initializing an image guided surgery, according to certain embodiments.

FIG. 2 illustrates an example workflow 200 for automatically initializing an image guided surgery, according to certain embodiments. The workflow 200 may be performed by the automated image guidance tool 115. In the depicted embodiment, the eye detection component 120 receives one or more intra-op images 180 of a scene. As noted, the intra-op image(s) 180 may be captured by the imaging device 150.

The eye detection component 120 is generally configured to detect when the patient's eye 160 is in the scene and has a particular arrangement suitable for performing image registration. For example, while one or more visualization parameters (e.g., focus, magnification, illumination, position of the eye with respect to the visualization tool 140, etc.) are being adjusted, the eye detection component 120 can evaluate the intra-op image(s) 180 using an eye detection algorithm 220 to detect when the patient's eye has the particular arrangement. The visualization parameter(s) may be manually adjusted by a user (e.g., surgeon or surgical staff member), adjusted via a hands-free user device (e.g., foot pedal), or automatically adjusted by the visualization tool 140.

In certain embodiments, the eye detection algorithm 220 may determine that the patient's eye is present within an intra-op image 180 based on whether the intra-op image 180 includes one or more features (or landmarks) associated with eye tissue/structures. Such features can include, for example, but are not limited to, speculum, limbus, centration point, etc. In certain embodiments, the eye detection algorithm 220 can determine an arrangement of the patient's eye within an intra-op image 180 based on one or more of the features. For example, the eye detection algorithm 220 may determine a position of the patient's eye with respect to the visualization tool 140, based on the speculum. In another example, the eye detection algorithm 220 may determine a scale of the patient's eye (relative to a scale of the reference image 190), based on the limbus. In yet another example, the eye detection algorithm 220 may determine a centration point based on a center of the limbus.

In certain embodiments, the eye detection algorithm 220 generates positioning feedback 230 based on the evaluation of the intra-op image(s) 180. The positioning feedback 230 may include information regarding the position of the patient's eye 160 (relative to the visualization tool 140), orientation of the patient's eye 160, centration point, etc. In certain embodiments, the positioning feedback 230 may be displayed using augmented reality in the FOV of the visualization tool 140. The positioning feedback 230 may provide guidance to the user in terms of how to adjust one or more parameters of the visualization tool 140 (e.g., position of the visualization tool 140 with respect to the patient's eye 160, focus, magnification, illumination, etc.), how to center the patient's eye, and the like. For example, the positioning feedback 230 may be displayed to the user (via the visualization tool 140) while the user is adjusting the one or more parameters of the visualization tool 140 and/or positioning the patient's eye 160 within the scene.

As shown in FIG. 2, in certain embodiments, the eye detection algorithm 220 selects one of the intra-op images 180 that satisfies a predetermined condition as a candidate intra-op image 235. In an exemplary embodiment, the eye detection algorithm 220 may select, as the candidate intra-op image 235, an intra-op image 180 having a threshold number of detectable features. In another exemplary embodiment, the eye detection algorithm may select the first intra-op image 180 in which a limbus and/or speculum is detected.

In certain embodiments, the eye detection algorithm 220 sends the candidate intra-op image 235 to the registration component 125 to trigger an initiation of an image registration of the candidate intra-op image 235 and the reference image 190. As noted, the image registration may generally be performed as part of the initialization of the image guided surgery. The registration component 125 includes one or more registration algorithms 240. Examples of the registration algorithms 240 can include image processing-based registration algorithms, machine learning based registration algorithms, image-processing and machine learning based registration algorithms, etc.

In certain embodiments, as part of the image registration, the registration component 125 generates transformation information 255, which may include at least one of scaling information, translation information (including centration information), and/or rotation information for transforming at least one of the candidate intra-op image 235 or the reference image 190. In an exemplary embodiment, the transformation information 255 includes at least one of scaling information, translation information (including centration information), and/or rotation information for transforming the reference image 190.

The registration component 125 sends the transformation information 255 to the overlay component 130, which includes an overlay generator 260 and a validation tool 265. The overlay generator 260 is generally configured to generate overlay content 275, based on the transformation information 255. In certain embodiments, the overlay content 275 includes an overlay of the candidate intra-op image 235 and the reference image 190, aligned using the transformation information 255. For example, the overlay content 275 may include a (transformed) candidate intra-op image and/or a (transformed) reference image transformed according to the transformation information 255.

The validation tool 265 is generally configured to verify that the transformation information 255 satisfies a predetermined level of quality. For example, in certain embodiments, the validation tool 265 may perform image registration using multiple different registration algorithms 240 and verify that the respective transformation information 255 output from each registration algorithm is the same or similar (e.g., the difference between the respective transformation information 255 is within a threshold). In certain embodiments, the validation tool 265 may validate the transformation information 255 prior to generation of the overlay content 275.

Note that FIG. 2 illustrates a reference example configuration of a workflow 200 that can be used to automatically initialize an image guided surgery and that the workflow 200 may have other configurations consistent with the functionality described herein. For example, while the workflow 200 is described as being implemented with an eye detection component 120, a registration component 125, and an overlay component 130, the workflow 200 may be implemented using any number of components (e.g., a single component, multiple components, etc.).

FIG. 3 is a flowchart of an example method 300 for automatically initializing an image guided surgery, according to certain embodiments. The method 300 may be performed by an automated image guidance tool (e.g., automated image guidance tool 115).

Method 300 enters at block 305, where the automated image guidance tool monitors a surgical scene in an intra-operative environment via a camera device (e.g., imaging device 150). As noted, the camera device may be configured to continuously capture a number of intra-op images (e.g., intra-op images 180) of the scene while a user (e.g., surgeon or surgical staff member) adjusts one or more parameters (e.g., focus, magnification, illumination, position with respect to the patient's eye, etc.) of a visualization tool (e.g., visualization tool 140) and/or a center position of the patient's eye.

At block 310, the automated image guidance tool detects an eye of a patient (e.g., patient's eye 160) in the intra-operative environment, based on the monitoring. For example, the automated image guidance tool can employ an eye detection algorithm to evaluate whether one or more intra-operative images include one or more features indicative of eye tissue/structures.

At block 315, the automated image guidance tool automatically initializes an image guided surgery using one of the images of the eye captured within the intra-operative environment and a reference image (e.g., reference image 190) of the eye. In certain embodiments, automatically initializing an image guided surgery includes initiating an image registration procedure with the one of the images captured within the intra-operative environment and the reference image. In certain embodiments, the automated image guidance tool may select one of the intra-op images that satisfies a predetermined condition as the image to use for the image registration procedure. The predetermined condition may include a threshold number of features detected within the intra-op image, a first image in which a predefined feature(s) is detected, etc.

At block 320, the automated image guidance tool presents overlay content generated from the registration procedure within the intra-operative environment. In certain embodiments, the overlay content may include an overlay of the selected intra-op image and the reference image aligned using a set of transformation information (e.g., transformation information 255) generated form the registration procedure. The overlay content may be presented (or displayed) onto the scene via the visualization tool (e.g., in the FOV of the visualization tool).

FIG. 4 is a flowchart of another method 400 for automatically initializing an image guided surgery, according to certain embodiments. The method 400 may be performed by an automated image guidance tool (e.g., automated image guidance tool 115).

Method 400 enters at block 405, where the automated image guidance tool monitors a scene in an intra-operative environment via a camera device (e.g., imaging device 150). The operations in block 405 may be similar to the operations in block 305 of method 300 in FIG. 3.

The operations in one or more of the blocks 410, 415, 420, 425, 430, 435, 440, and 445 may be performed for each (intra-op) image captured during the monitoring. At block 410, the automated image guidance tool determines whether an eye is detected within a captured image. For example, the automated image guidance tool may determine that an eye is present (as opposed to another structure or material) when a speculum and/or limbus is detected within the captured image.

If, at block 410, an eye is not detected within the captured image, the method 400 proceeds to process another captured image. If, at block 410, an eye is detected within the captured image, then, at block 415, the automated image guidance tool determines a set of features associated with the eye from the image. The set of features may include one or more landmarks (or points of the eye), examples of which can include, speculum, limbus, centration point, scale of the limbus, blood vessel(s), etc.

At block 420, the automated image guidance tool determines whether the features satisfy one or more predetermined conditions. The predetermined condition(s) at block 420 may be based on a threshold number of features, a predefined scale of the limbus (e.g., based on the scale of the limbus within the reference image), a predefined centration point. If, at block 420, the automated image guidance tool determines that the features do not satisfy the predetermined conditions (e.g., a threshold number of features were not detected, eye is in an incorrect arrangement due to at least one of an incorrect position, scale and/or centration point), then the automated image guidance tool, at block 425, provides positioning feedback regarding the eye to a user (e.g., surgeon or surgical staff member) and proceeds to process another captured image.

If, at block 420, the automated image guidance tool determines that the features do satisfy the predetermined conditions, then the automated image guidance tool, at block 430, performs a registration procedure with the image and a reference image to generate a set of transformation information (e.g., transformation information 255). At block 435, the automated image guidance tool determines whether the transformation information satisfies a predetermined condition(s). For example, the predetermined condition(s) at block 435 may be associated with a threshold level of quality. In certain embodiments, the automated image guidance tool may determine that the transformation information satisfies the predetermined condition when multiple registration algorithms output the same set or similar set of transformation information.

If, at block 435, the automated image guidance tool determines the transformation information does satisfy the predetermined condition(s), then, at block 440, the automated image guidance tool generates and presents overlay content, based on the transformation information. On the other hand, if, at block 435, the automated image guidance tool determines the transformation information does not satisfy the predetermined condition(s), then, at block 445, the automated image guidance tool determines whether a manual trigger is satisfied. For example, in certain embodiments, the automated image guidance tool may determine that the manual trigger is satisfied when a number of image registration attempts have been initiated.

If, at block 445, the automated image guidance tool determines that the manual trigger is not satisfied, then the method 400 proceeds to block 425, described above. If, at block 445, the automated image guidance tool determines that the manual trigger is satisfied, then the method 400 may exit. In certain embodiments, in response to the manual trigger, the automated image guidance tool may prompt the user to provide input regarding at least a portion of the transformation information. For example, the automated image guidance tool may prompt the user to adjust a rotation of at least one of the intra-op image or the reference image for the image guided surgery. In certain embodiments, the user may provide the input via a hands-free user device (e.g., foot pedal).

Figure 5:
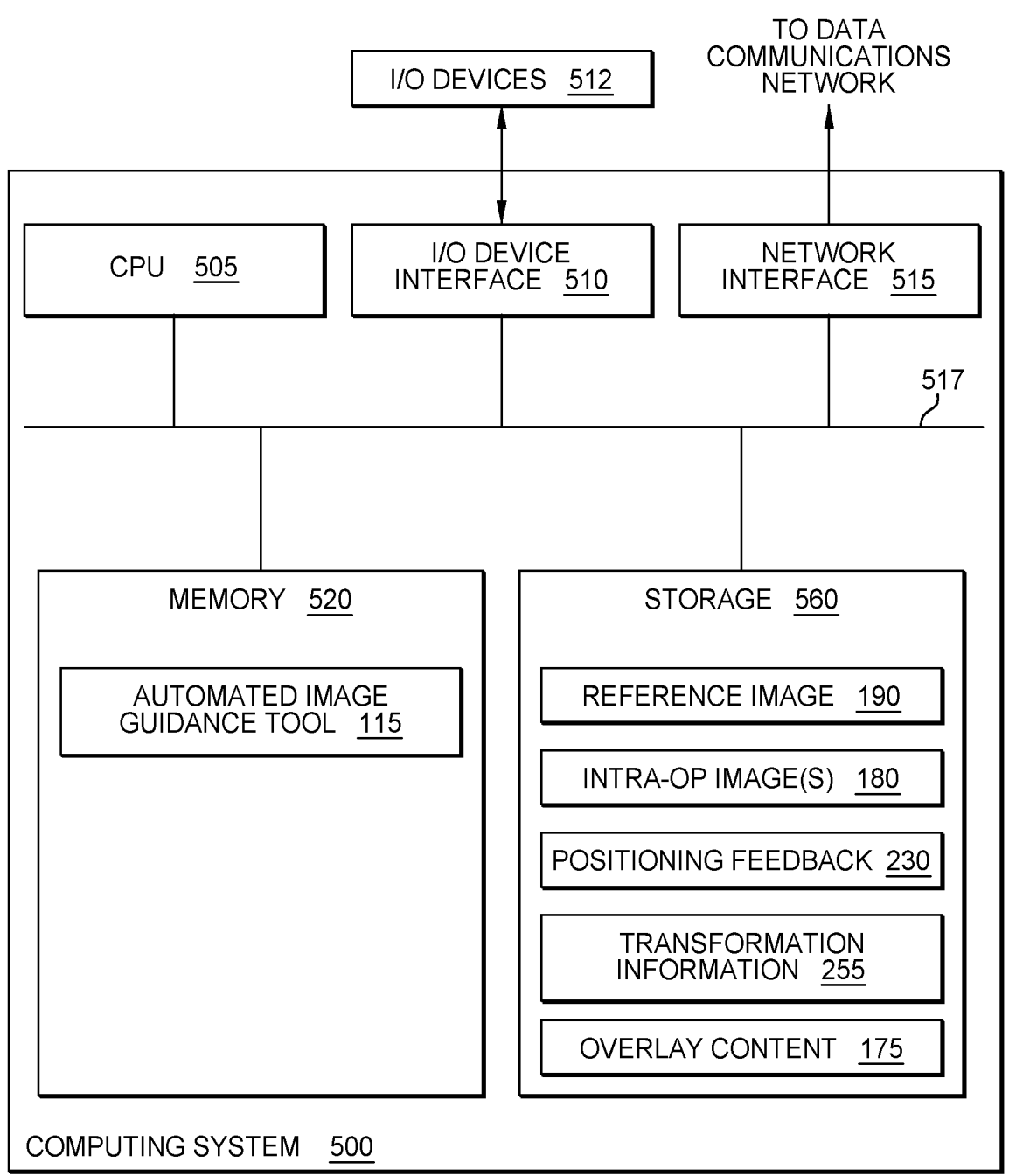
FIG. 5 illustrates an example computing system for automatically initializing an image guided surgery, according to certain embodiments.

FIG. 5 illustrates an example computing system 500 configured to automatically initialize an image guided surgery, according to certain embodiments. As shown, the computing system 500 includes, without limitation, a processing unit 505, a network interface 515, a memory 520, and storage 560, each connected to a bus 517. The computing system 500 may also include an I/O device interface 510 connecting I/O devices 512 (e.g., keyboard, display and mouse devices) to the computing system 500. The computing system 500 is generally under the control of an operating system (not shown). Examples of operating systems include the UNIX operating system, versions of the Microsoft Windows operating system, and distributions of the Linux operating system. (UNIX is a registered trademark of The Open Group in the United States and other countries. Microsoft and Windows are trademarks of Microsoft Corporation in the United States, other countries, or both. Linux is a registered trademark of Linus Torvalds in the United States, other countries, or both.) More generally, any operating system supporting the functions disclosed herein may be used.

The processing unit 505 can include one or more central processing units (CPUs) and/or one or more graphics processing units (GPUs). The processing unit 505 retrieves and executes programming instructions stored in the memory 520 as well as stored in the storage 560. The bus 517 is used to transmit programming instructions and application data between the processing unit 505, I/O device interface 510, storage 560, network interface 515, and memory 520. Note, processing unit 505 is included to be representative of a single CPU, multiple CPUs, a single CPU having multiple processing cores, a single GPU, multiple GPUs, a single GPU having multiple processing cores, or any combination thereof. The memory 520 is generally included to be representative of a random access memory. The storage 560 may be a disk drive or flash storage device. Although shown as a single unit, the storage 560 may be a combination of fixed and/or removable storage devices, such as fixed disc drives, removable memory cards, optical storage, network attached storage (NAS), or a storage area-network (SAN). Illustratively, the memory 520 includes the automated image guidance tool 115, which is discussed in greater detail above. Further, storage 560 includes a reference image 190, intra-op image(s) 180, positioning feedback 230, transformation information 255, and overlay content 175, described above.

In summary, certain embodiments of the present disclosure allow for reducing or fully removing manual interactions that are typically required by conventional systems to start an image guided surgery. By reducing or removing these manual interactions, embodiments can significantly improve the surgeon's experience during a surgical procedure, lower the barrier to adoption of image guidance technology, reduce time and/or space associated with performing image guided surgery, etc.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a c c, b-b, b-b-b, b-b-c, c-c, and c-c-c or any other ordering of a, b, and c).

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

Within a claim, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for." The word "exemplary" is used herein to mean "serving as an example, instance, or illustration." Any aspect described herein as "exemplary" is not necessarily to be construed as preferred or advantageous over other aspects.

What is claimed is:

1. An ophthalmic system comprising:
a first imaging device adapted to capture a plurality of images of a scene within an intra-operative environment;
a second imaging device adapted to visualize the scene;
a memory comprising executable instructions; and
a processor in data communication with the memory and configured to execute the executable instructions to:
monitor the scene using the plurality of images captured by the first imaging device;
upon detecting an eye of a user within a first image of the plurality of images, automatically initialize an image-guided surgery, comprising initiating a registration procedure to generate a set of transformation information, based at least in part on the first image and a reference image of the eye of the user;
generate a set of overlay content based on the set of transformation information, wherein the set of overlay content comprises (i) a transformed first image or (ii) a transformed reference image; and
present the overlay content onto the scene via the second imaging device.

2. The ophthalmic system of claim 1, wherein the processor is further configured to execute the executable instructions to provide feedback on a position of the eye, based on the monitoring.

3. The ophthalmic system of claim 2, wherein the feedback is provided while the plurality of images are being captured by the first imaging device.

4. The ophthalmic system of claim 1, wherein the transformation information comprises at least one of: (i) scaling information, (ii) translation information, or (iii) rotation information.

5. The ophthalmic system of claim 1, wherein detecting the eye of the user comprises detecting, via an eye detection algorithm, a set of features within the first image associated with ocular structures.

6. The ophthalmic system of claim 5, wherein the set of features comprises at least one of a speculum or a limbus.

7. The ophthalmic system of claim 1, wherein the processor is further configured to execute the executable instructions to validate the set of transformation information prior to generation of the overlay content.

8. The ophthalmic system of claim 1, wherein:
the first image is an intra-operative image; and
the reference image is a pre-operative image.

9. A computer-implemented method comprising:
monitoring a scene in an intra-operative environment using a plurality of images captured by a first imaging device;
upon detecting an eye of a user within a first image of the plurality of images, automatically initializing an image-guided surgery, wherein automatically initializing the image-guided surgery comprises initiating a registration procedure to generate a set of transformation information, based at least in part on the first image and a reference image of the eye of the user;
generating a set of overlay content based on the set of transformation information, wherein the set of overlay content comprises (i) a transformed first image or (ii) a transformed reference image; and
presenting the overlay content onto the scene via a second imaging device.

10. The computer-implemented method of claim 9, further comprising providing feedback on a position of the eye, based on the monitoring.

11. The computer-implemented method of claim 10, wherein the feedback is provided while the plurality of images are being captured by the first imaging device.

12. The computer-implemented method of claim 9, wherein the transformation information comprises at least one of: (i) scaling information, (ii) translation information, or (iii) rotation information.

13. The computer-implemented method of claim 9, wherein detecting the eye of the user comprises detecting, via an eye detection algorithm, a set of features within the first image associated with ocular structures.

14. The computer-implemented method of claim 13, wherein the set of features comprises at least one of a speculum or a limbus.

15. The computer-implemented method of claim 9, further comprising validating the set of transformation information prior to generation of the overlay content.

16. The computer-implemented method of claim 9, wherein:
the first image is an intra-operative image; and
the reference image is a pre-operative image.

17. A non-transitory computer-readable medium having computer executable instructions stored thereon, the computer executable instructions being executable by one or more processors to perform an operation comprising:
monitoring a scene in an intra-operative environment using a plurality of images captured by a first imaging device;
upon detecting an eye of a user within a first image of the plurality of images, automatically initializing an image-guided surgery, wherein automatically initializing the image-guided surgery comprises initiating a registration procedure to generate a set of transformation information, based at least in part on the first image and a reference image of the eye of the user;
generating a set of overlay content based on the set of transformation information, wherein the set of overlay content comprises (i) a transformed first image or (ii) a transformed reference image; and
presenting the overlay content onto the scene via a second imaging device.

18. The non-transitory computer-readable medium of claim 17, the operation further comprising providing feedback on a position of the eye, based on the monitoring.

19. The non-transitory computer-readable medium of claim 18, wherein the feedback is provided while the plurality of images are being captured by the first imaging device.

20. The non-transitory computer-readable medium of claim 17, wherein:

detecting the eye of the user comprises detecting, via an eye detection algorithm, a set of features within the first image associated with ocular structures; and the set of features comprises at least one of a speculum or a limbus.

<center>* * * * *</center>